(12) United States Patent
Rolston et al.

(10) Patent No.: US 8,465,963 B2
(45) Date of Patent: Jun. 18, 2013

(54) GRASS ENDOPHYTE ENHANCED ATTRIBUTES

(75) Inventors: Maurice Philip Rolston, Christchurch (NZ); Wayne Roydon Simpson, Palmerston North (NZ)

(73) Assignee: Grasslanz Technology Ltd., Palmerston North (NZ)

( * ) Notice: Subject to any disclaimer, the term of this patent is extended or adjusted under 35 U.S.C. 154(b) by 789 days.

(21) Appl. No.: 11/917,137

(22) PCT Filed: Aug. 4, 2006

(86) PCT No.: PCT/NZ2006/000202
§ 371 (c)(1),
(2), (4) Date: Jun. 30, 2010

(87) PCT Pub. No.: WO2007/021200
PCT Pub. Date: Feb. 22, 2007

(65) Prior Publication Data
US 2010/0278780 A1    Nov. 4, 2010

(30) Foreign Application Priority Data
Aug. 16, 2005 (NZ) ........................ 541606

(51) Int. Cl.
*C12N 1/14* (2006.01)
*A01N 63/00* (2006.01)

(52) U.S. Cl.
USPC .................. 435/254.1; 435/911; 504/117

(58) Field of Classification Search
None
See application file for complete search history.

(56) References Cited

U.S. PATENT DOCUMENTS

| | | | |
|---|---|---|---|
| 5,720,972 A | 2/1998 | Munday | |
| 6,111,170 A * | 8/2000 | Latch et al. | 800/320 |
| 6,416,782 B1 | 7/2002 | Maas | |
| 2005/0150024 A1 | 7/2005 | West et al. | |

FOREIGN PATENT DOCUMENTS

| | | |
|---|---|---|
| GB | 2333451 | 7/1999 |
| NZ | 228233 | 9/1990 |
| NZ | 233083 | 3/1991 |
| NZ | 241391 | 4/1994 |
| NZ | 278977 | 3/1997 |
| RU | 2201678 C2 | 4/2003 |
| WO | WO 92/05776 | 4/1992 |
| WO | WO 01/87273 | 11/2001 |
| WO | WO 02/13616 | 2/2002 |
| WO | WO 02/089763 | 11/2002 |
| WO | WO 2004/106487 | 12/2004 |

OTHER PUBLICATIONS

Bluett et al., "Effects of a novel ryegrass endophyte on pasture production, dairy cow milk production, and calf liveweight gain", *Australian Journal of Experimental Agriculture* (2005) 45(1):11-19.

Hill et al., "Endophyte viability in seedling tall fescue treated with fungicides", *Crop Science* (2000) 40(5): 1490-1491.

Meriaux et al., "Effect of fungicides and heat treatment on seed germination of endophyte infected perennial ryegrass", Proceedings of the 19th General Meeting of the European Grassland Federation, La Rochelle, France, May 27-30, 2002; *Grassland Science in Europe* 7: 536-537.

Park et al., "Isolation and characterization of *Burkholderia cepacia* EP215, An Endophytic Bacterium Showing a Potent Antifungal Activity Against *Colletrotrichum* species", *Korean J. of Microbiology and Biotechnology* (2005) 33(1): 16-23. (Abstract Only).

Rolston et al., "Tolerance of AR1 *Neotyphodium* endophyte to fungicides used in perennial ryegrass seed production", *NZ Plant Protection* (Aug. 2002) 55: 322-326.

Saiga et al., "Endophyte removal by fungicides from ramets of perennial ryegrass and tall fescue", *Grassland Science* (2003) 48(6): 504-509.

Siegel et al., "A fungal endophyte of tall fescue: evaluation of control methods", *Phytopathology* (1984) 74(8): 937-941.

Timper et al., "Response of *Pratylenchus* spp. in tall fescue infected with different strains of the funfal endophyte *Neotyphoidum coenophialum*" *Nematology* (2005) 7(1): 105-110.

Rolston, M.P. and Agee, C. 2007. Delivering Quality Seed to Specification—the USA and NZ Novel Endophyte Experience. Proceedings of the 6th International Symposium on Fungal Endophytes of Grasses. Grasslands Research and Practice Series No. 13: 229-231.

* cited by examiner

*Primary Examiner* — Vera Afremova
(74) *Attorney, Agent, or Firm* — Knobbe Martens Olson & Bear LLP

(57) ABSTRACT

Described is the method and use of AR584 endophyte (AGAL deposit no. NM98/04676 dated 12 May 1998) or variations in endophyte as exemplified by AR584, to produce a grass cultivar and AR584 combination wherein the plant or a part thereof produced by the combination retains viable AR584 endophyte after treatment with fungicide and/or after being subjected to elevated temperature or humidity.

19 Claims, 2 Drawing Sheets

GRASS ENDOPHYTE ENHANCED ATTRIBUTES

RELATED APPLICATIONS

This application is a U.S. National Phase of International Application No. PCT/NZ2006/000202, filed Aug. 4, 2006, designating the U.S. and published on Feb. 22, 2007 as WO 2007/021200, which claims priority to New Zealand Patent Application No. 541606, filed on Aug. 16, 2005. The content of these applications are incorporated herein by reference in their entireties.

TECHNICAL FIELD

The invention relates to grass endophyte enhanced attributes. More specifically, the invention relates to an endophyte with improved fungicide resistance and stability when in combination with a cultivated plant or part thereof.

BACKGROUND ART

It is known from New Zealand patent specification 233,083 that synthetic combinations of endophyte/herbage cultivars can be made which are resistant to pests and can be less toxic to grazing animals than naturally occurring combinations. These selected properties may be achieved by selecting synthetic combinations which produce relatively high levels of peramine and relatively low levels of or no lolitrem B in ryegrass.

U.S. Pat. No. 6,111,170 (the '170 patent), describes findings that selected endophytes of the genus *Neotyphodium* form stable synthetic combinations with tall fescue hosts (*Festuca arundinacea*). The combinations described have improved resistance to invertebrate pests as compared to tall fescue cultivars that do not contain such endophytes. The particular strains of endophyte described in the '170 patent include AR501, AR502, AR510, AR542, AR572, AR577 and AR584. This patent does not however describe, nor suggest other attributes of these endophytes and their combinations beyond improved pest resistance and reduced toxicity.

Russian patent abstract, RU2201678C2 describes a biopreparation for protecting plants against fungus and bacterial diseases. The biopreparation is based upon live cells and spores of endophytic bacterium *Bacillus subtilis*. This bacterium has a high antagonistic activity to agents of fungus and bacterial diseases in vegetable, grain and fruit cultures. No description is made regarding use of the bacterium in grasses. It is also not obvious from this abstract that the bacterium described is resistant to fungicides. The description merely makes reference to the bacterium preventing fungal infection of the plant in effect acting as a fungicide itself.

Meriaux et al describes the viability of ryegrass (*Lolium perenne*) seed infected with *Neotyphodium* endophyte after treatment with fungicides. The fungicides used were prochloraze (prochloraz), triticonazole, bitertanol, and fluquinconazole administered at two doses or heat treated (oven treatment at 60 or 80° C.). Seed germination is described as being effected for treatment with prochloraze (1 g/kg), triticonazole (5 and 10 g/kg) and heat treatment at 80° C. No reference is made or suggested towards endophyte viability or viability (seed or endophyte) when combined with cultivated grasses. It is the inventor's experience that seed viability and endophyte viability are two very different issues with seeds often retaining viability for longer than endophytes.

Rolston et al describes fungicide treatment effects on AR1 endophyte and ryegrass combinations. AR1 is a *Neotyphodium* species endophyte that has a different alkaloid profile to AR584 in that AR1 does not produce loline alkaloids and may produce terpendoles differently to AR584. The publication notes that AR1 endophyte viability was not affected by the fungicide treatments including triazole and strobilurin fungicides. It is the inventor's experience that it is not obvious that a property noted for one endophyte in one type of plant would also exhibit the same properties with another endophyte or plant. Anecdotal evidence exists showing that endophyte strain and plant species may result in very different results. One reason for the variation is that different endophytes give different attributes to grass endophyte combinations. One reason for the variation is that different endophytes have different levels and types of alkaloid profile. As a result different endophytes in combination with different grasses have variable properties. In addition, different species of grass also influence properties of combinations with endophytes.

Saiga et al describes the effects of *Neotyphodium* endophytes on plant characteristics including fungicide soak treatments. The fungicide, benomyl (benzimidazole group) is described as being effective in killing endophyte in both perennial ryegrass and tall fescue. Triforine (amide group) fungicide was effective in tall fescue and effective in some perennial ryegrass plants. Thiophanate-methyl (benzimidazole precursor fungicide) had little effect on endophyte in perennial ryegrass and had no effect on endophyte in tall fescue. The aim of the publication method is to remove endophytes altogether from the grass. As a result, particularly strong doses of fungicides are used and the grass is soaked in fungicide. No disclosure is made towards identification of endophytes with higher resistance to fungicides, or disclosure regarding stability.

Hill et al describes tall fescue cultivars containing endophytes including *Neotyphodium coenophialum*. The abstract discusses how to maintain viable endophyte in seedling plants by applying chloroneb (aromatic fungicide) and terrazole (thiazole group) fungicides during the first 7 to 21 days post germination. Hill et al does not identify endophytes with resistance to fungicides or identify AR584 as exhibiting any particular resistance. Further, the time period of analysis described is only post germination and only in seedling plants.

Park et al describes development of a microbial fungicide that utilises endophytic bacteria for the control of cucumber and red pepper anthracnoses caused by *Colletotrichum orbiculare* and *C. coccodes* and *C. acutatum*. Among 18 strains isolated, a bacterial strain EB215 isolated from cucumber roots displayed the most potent antifungal activity against *Colletotrichum* species. No mention is made regarding improved fungicide resistance due to endophyte, nor is usage in terms of grasses such as tall fescue.

Bluett et al describes a trial comparing various properties between ryegrass (*Lolium perenne*) infected with wild type endophyte, AR1 endophyte or no endophyte. AR1-infected ryegrass was found to produce similar pasture yields as wild endophyte-infected ryegrass, while offering small improvements in milk yield with no incidence of ryegrass staggers noted in grazing animals. No discussion is made on the endophyte effect with regard to fungicide treatment, endophyte stability or to the endophyte AR584 or tall fescue grass cultivars.

It should be appreciated by a person skilled in the art that an endophyte plant combination that has increased fungicide resistance would be of benefit to enhance existing turf and forage seed crop management practices. In addition, increased stability during transport would also be an advantage.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

For the purposes of this specification, the term 'endophyte' or grammatical variations thereof refer to fungi of *Neotyphodium* spp. living within cultivated grasses or axenic culture medium.

The term 'cultivated grasses' or grammatical variations thereof refer to varieties of grasses that have been created or selected intentionally and maintained through cultivation.

The term 'synthetic grass cultivar' refers to the grass cultivar being produced through selective breeding techniques including selection and development from an uncultivated population. For example, a synthetic grass cultivar refers to where— reproducible units are from a cross-pollinated crop. This could encompass clones or inbred grasses for example;

materials used are selected from their performance in combining ability or progeny tests;

the cultivar is constituted by random inter-mating of the units;

the units are maintained so that the synthetic can be reconstituted.

The term 'combination' or grammatical variations thereof refer to the combination of an endophyte and culturally improved grass varieties each of which have been isolated from nature, but the combination of which does not exist in nature.

The term 'plant or a part thereof' refers to the plant in entirety or selected portions of the plant during the plant life cycle such as the plant seed, shoots, roots, flowers, stems and the like. The term 'retain' or grammatical variations thereof in relation to endophytes refers to the ability of the endophyte to maintain a level of viability in combination with a host plant, or part thereof, at a level acceptable for a given circumstance or set of circumstances over a given period of time and under a given set of conditions. It should be appreciated by those skilled in the art that acceptable percentages for viability may vary depending on the generation or class of seed to which it relates as well as by varying industry standards.

The term 'viable' or grammatical variations thereof refer to the endophyte being capable of living, developing, or multiplying under favorable conditions in symbiotic relationship with a host plant or in axenic culture.

The term 'treatment with fungicide' refers to the combination being sprayed, powdered, infused or other methods of administration, by a fungicide containing composition.

The term 'fungicide' refers to substances that destroy or inhibit growth of fungi.

According to one aspect of the present invention there is provided the use of AR584 endophyte (AGAL deposit no. NM98/04676 dated 12 May 1998) or variations in endophyte as exemplified by AR584, to produce a grass cultivar and AR584 combination wherein the plant or a part thereof produced by the combination retains viable AR584 endophyte therein after treatment with fungicide.

According to a further aspect of the present invention there is provided a method of retaining endophyte viability in a plant or a part thereof after treatment with fungicide, produced by a combination a grass cultivar and endophyte combination, wherein the endophyte is AR584 endophyte (AGAL deposit no. NM98/04676 dated 12 May 1998) or variations in endophyte as exemplified by AR584.

The inventor's have unexpectedly found that AR584 endophyte exhibits an improved ability to resist fungicide treatments. It is envisaged that this attribute will have significant commercial benefit in farming. By way of example, standard farm turf or seed crop management calls for spraying of fungicide treatments to the turf or seed crop to avoid foliar and soil borne fungal diseases. A problem with existing grasses and grass endophyte combinations is that, fungicides commonly used in turf and seed crop management and control of unwanted fungal pathogens also tend to significantly reduce endophyte viability. As a result, the favourable properties noted for endophyte and grass combinations may be reduced or negated altogether. AR584 however has been noted by the inventors to have a resistance to standard commercial fungicides to an extent that means a farmer can spray to avoid foliar diseases and unwanted soil borne fungal pathogens and still retain adequate endophyte viability.

Preferably, at least a 50% or greater endophyte viability is retained after fungicide treatment.

Preferably, the fungicides used in treatment have systemic characteristics.

Preferably, the fungicides used in treatment have foliar disease control characteristics.

Preferably, the fungicide used in treatment has activity against soil borne fungicidal pathogens.

Preferably, fungicides used in treatment are selected from the triazole group, strobilurin group or combinations of these two fungicide groups.

Preferably, at least 60% or greater endophyte viability is retained after being subjected to treatment with triazole based fungicide.

Preferably, the combination retains at least 65% or greater endophyte viability, more preferably, greater than 80% viability, when subjected to a 50:50 wt/wt combination of triazole based fungicide and strobilurin based fungicide.

Preferably, the fungicide treatment is applied to the grass cultivar and endophyte combination at standard rates used in control of foliar diseases.

Preferably, triazole based fungicide treatment is applied as a spray at a rate of 1000 ml/ha. This is envisaged to be the equivalent to 250 g epiconazole/ha.

Preferably, strobilurin based fungicide treatment is applied as a spray at a rate of 1000 ml/ha. This is envisaged to be the equivalent to 250 g azoxystrobin/ha.

Preferably, the fungicide treatment is applied at early flowering of the grass cultivar and endophyte combination.

Preferably, the fungicide treatment is applied to the combination at early flowering and re-applied again at late flowering of the combination.

In preferred embodiments, the fungicide is applied as a spray although this should not be seen as limiting as the fungicide may be applied by other methods such as immersion, powders, dusting, gels or combinations thereof. It is envisaged that this could be applied to the plant or part thereof.

According to a further aspect of the present invention there is provided a use of AR584 endophyte (AGAL deposit no. NM98/04676 dated 12 May 1998) or variations in endophyte as exemplified by AR584, to produce a grass cultivar and AR584 combination wherein the plant or a part thereof produced by the combination retains viable AR584 endophyte therein after the combination is subjected to temperatures of between 15° C. and 55° C. for a time period of at least 3 days.

According to a further aspect of the present invention there is provided a method of retaining endophyte viability in a plant or a part thereof after treatment with fungicide, produced by a combination of a grass cultivar and endophyte combination, wherein the endophyte is AR584 endophyte (AGAL deposit no. NM98/04676 dated 12 May 1998) or variations in endophyte as exemplified by AR584, wherein the combination retains viable AR584 endophyte therein after the combination is subjected to temperatures of between 15° C. and 55° C. for a time period of at least 3 days.

According to a further aspect of the present invention there is provided a use of AR584 endophyte (AGAL deposit no. NM98/04676 dated 12 May 1998) or variations in endophyte as exemplified by AR584, to produce a grass cultivar and AR584 combination wherein the plant or a part thereof produced by the combination retains at least 60% or greater endophyte viability when the combination is subjected to a temperature of up to 40° C. and a relative humidity of up to 100% for at least a time period of 3 days.

According to a further aspect of the present invention there is provided a method of retaining endophyte viability in a plant or a part thereof after treatment with fungicide, produced by a combination of a grass cultivar and endophyte combination, wherein the endophyte is AR584 endophyte (AGAL deposit no. NM98/04676 dated 12 May 1998) or variations in endophyte as exemplified by AR584, wherein the combination retains at least 60% or greater endophyte viability when the combination is subjected to a temperature of up to 40° C. and a relative humidity of up to 100% for at least a time period of 3 days.

Preferably, the plant or a part thereof produced by the combination of the endophyte and grass cultivar combination as described above is further characterised by retaining endophyte viability when the grass and endophyte combination is subjected to temperatures above 20° C.

Preferably, the AR584 endophyte in the combination retains at least a 50% or greater endophyte viability.

Preferably, the endophyte viability is retained when the endophyte and plant or part thereof combination is subjected to temperatures of 35° C. to 45° C.

Preferably, endophyte viability is retained when the endophyte and plant or part thereof combination is subjected to temperatures of 40° C.

Preferably, endophyte viability is retained when the endophyte and plant or part thereof combination is subjected to a temperature increase as described over on a continuous basis. Preferably, endophyte viability is retained when the temperature is increased over time periods of at least 3 days.

Preferably, the plant or a part thereof produced by the endophyte and grass cultivar combination is further characterised by retaining endophyte viability when the grass and endophyte combination is subjected to a relative humidity of 70% or greater.

Preferably, the endophyte viability is retained when the combination is subjected to a relative humidity of 70% or greater for at least 3 days.

Preferably, the plant or a part thereof produced by the endophyte and grass cultivar combination is able to maintain viability when subjected to relative humidity of up to 100%. Preferably, endophyte viability is retained when the endophyte and plant or part thereof combination is subjected to a humidity increase as described over on a continuous basis. Preferably, endophyte viability is retained when the humidity is increased over time periods of at least 3 days.

Preferably, at least 75% or greater endophyte viability is retained.

According to a further aspect of the present invention there is provided a use of AR584 endophyte (AGAL deposit no. NM98/04676 dated 12 May 1998) or variations in endophyte as exemplified by AR584, to produce a grass cultivar and AR584 combination characterised in that the plant or a part thereof produced by the combination:
(a) retains at least 60% or greater endophyte viability when the combination is subjected to a temperature of up to 40° C. and a relative humidity of up to 100% for at least a time period of 3 days; and,
(b) retains at least a 50% or greater endophyte viability after treatment with fungicide.

According to a further aspect of the present invention there is provided a method of retaining endophyte viability in a plant or a part thereof after treatment with fungicide, produced by a combination of a grass cultivar and endophyte combination, wherein the endophyte is AR584 endophyte (AGAL deposit no. NM98/04676 dated 12 May 1998) or variations in endophyte as exemplified by AR584, wherein the combination:
(a) retains at least 60% or greater endophyte viability when the combination is subjected to a temperature of up to 40° C. and a relative humidity of up to 100% for at least a time period of 3 days; and,
(b) retains at least a 50% or greater endophyte viability after treatment with fungicide.

The inventors have also unexpectedly found that AR584 endophyte has a surprisingly high tolerance to elevated temperatures and humidities allowing it to remain viable within a plant or part thereof for extended periods of time in such conditions. This attribute is of commercial benefit where plants or parts thereof are transported as few special treatments such as refrigeration are required therefore also reducing the cost of transport.

Preferably, the plant or part thereof is the entire plant or selected portions of the plant. It is envisaged that this may encompass the plant seed(s), shoot(s), leaves, stem(s), flower(s), root(s) and combinations thereof.

Preferably, the plant or part thereof is a seed or seeds.

Preferably, the grass cultivar is selected from one or more tall fescue plant varieties.

Preferably, this may be selected from the group including: Grasslands Flecha, Grasslands Advance, Kentucky 31, Georgia 5, Jesup, Jackal, Quantum, and combinations thereof.

Preferably, the combination is produced by inoculating the grass cultivar with an axenic culture of the endophyte.

Preferably, the combination is produced by crossing the endophyte/grass cultivar combination with an endophyte free grass cultivar to form a grass cultivar infected with endophyte. Preferably, the grass cultivar is a synthetic grass cultivar.

It should be appreciated from the above description that there is provided new uses and methods for AR584 strain endophyte. In particular, the plant or part thereof produced by the combination of AR584 endophyte and a grass cultivar has significant new and unexpected advantages including an enhanced level of resistance to fungicides commonly used to prevent foliar diseases in grass. This attribute means that a farmer can apply standard fungicides without need for any special handling.

The plant or part thereof also has a significantly improved stability compared to other existing endophyte/grass cultivar combinations with respect to retaining endophyte viability when the plant or part thereof is subjected to extremes of temperature and humidity. One major benefit from this attribute is in transport, for example of seeds, where viability may be reduced using existing endophyte/grass combinations due to poor handling practices or extremes in temperature and humidity experienced in certain climates and countries. One such example may be when quantities of seed are transported in the holds of ships across varying climatic zones in uncontrolled storage environments.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
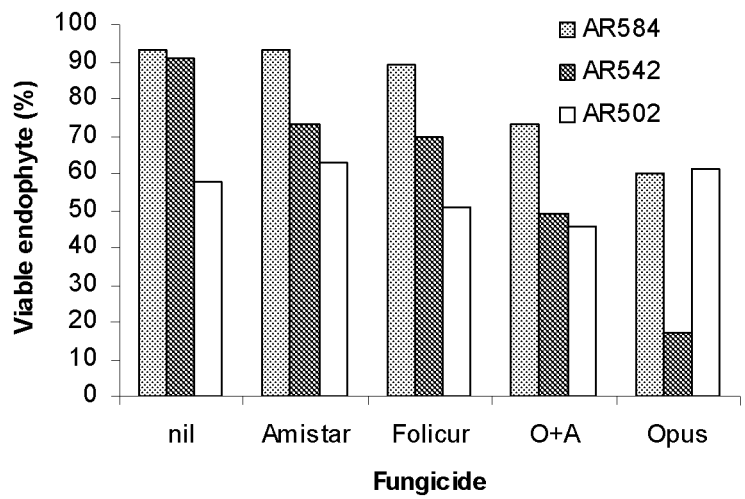
FIG. 1 is a graph comparing endophyte viability levels of AR584, AR542 and AR502 in combination with two different grass cultivars with five different fungicide treatments.
Figure 2:
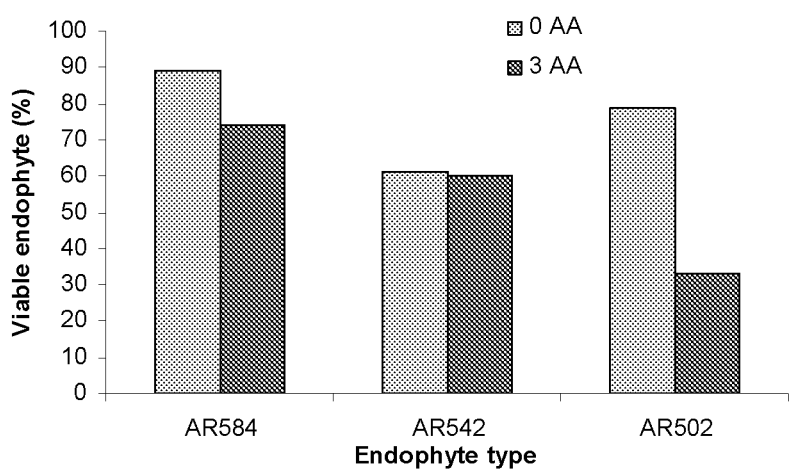
FIG. 2 is a graph comparing endophyte viability levels of AR584, AR542 and AR502 in combination with two different grass cultivars with either 0 days or 3 days accelerated aging (AA); and, FIG. 3 is a graph comparing viable endophyte levels for AR542 and AR584 in two different grass cultivars treated with three different fungicides treatments.

The invention methods and uses are now described with reference to trials completed by the inventors.

Trial 1
Introduction

The trial was undertaken to determine the tolerance of three endophytes (AR502, AR542 and AR584) to fungicides commonly used in grass seed production for the control of foliar diseases.

The fungicides evaluated belong to two different chemical groups. The first group relate to triazole fungicides including:
Opus@ with active ingredient epiconazole and
Folicur@ with active ingredient tebuconazole.

The second group relate to the strobilurin fungicides including Amistar@ with active agent azoxystrobin.

It is the inventor's experience that the above chemical groups account for over 90% of the fungicides used in tall fescue grass production and management.

The accelerated aging (AA) process is a high temperature (40° C.) and high relative humidity (RH) (100% RH) treatment of seed to simulate long term storage effects. Based on prior trials, accelerated aging is a useful and accurate predictor of long term natural storage stability.

Methods
Field Trial

Plants of two tall fescue cultivars 'Jesup' and 'Georgia 5' were inoculated with endophyte and transplanted into trial plots. Each plot consisted of 4 plants of each cultivar, in rows 1.0 m apart. Treatments were replicated three times in a randomised block design.

Fungicides
Five fungicide treatments were evaluated as follows:
1. Control
   Nil fungicide;
2. Opus@
   Epiconazole 250 g active ingredient per liter, triazole group sprayed at the label rate of 1000 ml/ha;
3. Amistar@
   Azoxystrobin 250 g active ingredient per hectare, strobilurin group
4. Opus@ and Amistar@
   Opus@ at 500 ml/ha (half label rate) and Amistar@ 500 ml/ha and applied as a tank mix;
5. Folicur@
   1. Tebuconazole 430 g active ingredient per liter; triazole group at the label rate of 440 ml/ha.

The doses used were the approximate recommended label rates for use of the above products. It should be noted that growers commonly use less than the label rate particularly if they plan to apply the fungicide more than once. As a result, the dosing rates used in this trial present a significant challenge to endophyte viability.

Fungicides were applied twice during the trial to replicate normal turf practice. Applications were made at Zadocks Growth Score (GS) 69 (early flowering/anthesis) and at Zadocks growth score (GS) 71 (caryopsis water ripe). This timing of application was as per those recommended to growers and coincides with the period of most disease pressure in crops.

Accelerated Aging

Seeds were suspended on a fine mesh above water enclosed within plastic sealed containers and placed in an incubator set to maintain a temperature of approximately 40° C. and with the seed chamber controlled to 100% relative humidity.

Endophyte Assessment by Grow-Out Test

Six replicates (each of 48 seedlings) consisting of duplicates from each treatment, were raised in peat-based trays and grown in a greenhouse for at least 6 weeks before blotting.

Endophyte Detection

Cut tillers from the seedlings after 6 weeks growth were blotted on nitro-cellulose paper and developed using an antibody/antigen reaction.

The development process is completed by immersing nitrocellulose membrane sheets in blocking solution for at least two hours at room temperature. The blocking solution is composed of 2.42 g of Tris (hydroxymethyl) methylamine, 2.92 g of NaCl, 5 g of non-fat milk powder and 10 ml HCl (1 M) in 1 L of water that has been passed through a reverse osmosis (RO) system. The pH of the solution is 7.5. During the immersion, any unbound site prior to the application of primary antibody is blocked.

After removing the blocking solution, 25 ml of fresh blocking solution per sheet is added along with 25 µl of primary antibody per sheet. The sheets are soaked overnight at 4° C. and shaken to keep the solution moving over the sheets. The next day, the blocking solution and primary antibody are removed and the sheets are rinsed several times with fresh blocking solution. Afterwards, the sheets are soaked and shaken for two hours at room temperature in 25 ml of fresh blocking solution with 12.5 µl of secondary antibody added. An enzyme is conjugated to this secondary antibody. Subsequently, blocking solution and the secondary antibody are decanted off and the sheets are rinsed by fresh blocking solution.

In order to develop the colour that allows endophyte identification, the nitrocellulose membranes are immersed into chromogen. This product is prepared by dissolving 75 mg of Fast Red in 12.5 ml of Tris buffer (For one liter of RO water, the Tris buffer is composed of 24.2 g of Tris (hydroxymethyl) methylamine (pH: 8.2)) per sheet and by dissolving separately 12.5 mg of napthol as-mx phosphate in 12.5 ml Tris buffer per sheet and these solutions combined. The sheets are incubated on shaker for 15 minutes. At the end of the 15 minutes, the chromogen is removed and the sheets are rinsed in water that has been passed through a reverse osmosis system. The sheets are then ready to be read.

Statistical Analysis

Data analysis was undertaken using a statistical package—GenStat. Version 7.

Results

Endophyte Effect

The average viable endophyte level of AR584 endophyte was significantly higher (P<0.001) than AR542 and AR502 for both fungicide treatment and accelerated aging experiments. AR584 averaged 81% viable endophyte after all treatments, while AR542 and AR502 averaged 60 and 56% respectively (Table 1).

The three endophytes were also noted as behaving differently between the main treatment variables: endophyte x cultivar; endophyte x accelerated aging (AA) and endophyte x fungicide (Table 1).

TABLE 1

Viable endophyte comparison of three endophyte strains (AR584; AR542 and AR502). Each value is averaged across two cultivars, two accelerated aging treatments, five fungicides and six repetitions).

| Endophyte | E + % |
|---|---|
| AR584 | 81 |
| AR542 | 60 |
| AR502 | 56 |
| LSD 5% | 5.1 |
| F probability | |
| Endophyte | <0.001 |
| Endophyte x cultivar | 0.005 |
| Endophyte x accelerated aging | <0.001 |
| Endophyte x fungicide | <0.001 |

Fungicide Effect

The two fungicides significantly reduced the level of viable endophyte (means of all other treatments) from 92% in the nil fungicide treatment to 61% for the Opus@ and Amistar@ mix; and 38% for the Opus@ only treatment (Table 2).

The data points to epiconazole as being the component most significantly reducing viable endophyte levels.

TABLE 2

Effect of fungicides on viable endophytes (data means averaged across two endophytes, two cultivars and six repetitions).

| Fungicide | E + % |
|---|---|
| nil | 81 |
| Amistar ® | 76 |

TABLE 2-continued

Effect of fungicides on viable endophytes (data means averaged across two endophytes, two cultivars and six repetitions).

| Fungicide | E + % |
|---|---|
| Folicur ® | 70 |
| Opus ® + Amistar ® | 61 |
| Opus ® | 45 |
| LSD 5% | 6.6 |
| F probability | |
| Fungicide | <0.001 |
| Fungicide x endophyte | <0.001 |

Endophyte and Fungicide Interaction

The endophyte and fungicide interaction as shown in Table 1 is further broken down in Table 3 below.

It is the inventor's unexpected findings that the interaction appears to arise because AR584 is significantly more tolerant of the two fungicides compared to the control and other endophyte combinations tested.

With the Opus@ and Amistar@ mixture treatment, AR584 had at least a 50% higher endophyte viability compared to other endophytes (73% viable endophyte compared to 49% in AR542). For Opus@ only treatments, AR584 had more than three times the level of viable endophyte compared to AR542. The interaction is shown in more detail in FIG. 1.

TABLE 3

AR584 and AR542 viable endophyte for fungicide treatments (means of two cultivars accelerated aging treatments and six repetitions).

| | Endophyte | | |
|---|---|---|---|
| | AR584 | AR542 | AR502 |
| Fungicide | Endophyte Viability [%] | | |
| Nil | 93 | 91 | 58 |
| Amistar | 93 | 73 | 63 |
| Folicur | 89 | 70 | 51 |
| Opus + Amistar | 73 | 49 | 46 |
| Opus | 60 | 17 | 61 |
| LSD 5% | | 11.3 | |

Cultivar Effect

There was a small cultivar effect, with Georgia 5 cultivar having higher endophyte levels than Jesup cultivar following fungicide treatments (Table 4). The cultivar and endophyte interaction was statistically significant.

TABLE 4

Viable endophyte for two cultivars (means averaged for three endophytes, five fungicides and six repetitions).

| Cultivar | Endophyte Viability [%] |
|---|---|
| Georgia 5 | 68 |
| Jesup | 63 |
| LSD 5% | 5 |
| F probability | |
| Cultivar | 0.02 |
| Cultivar x Endophyte | 0.005 |

Accelerated Aging

Three days of accelerated aging were tested to determine endophyte viability levels for AR584, AR542 and AR502 (Table 5).

The results found show that AR502 appears to be very sensitive to the accelerated aging treatment (Table 5 and FIG.

2) and AR584 has a significantly improved resistance to the elevated temperature and humidity.

TABLE 5

Effect of 0 or 3 days accelerated aging (AA) on viable endophyte (means of two cultivars, five fungicides and 6 reps).

| Endophyte | Days accelerated aging | |
|---|---|---|
| | 0 AA | 3 AA |
| AR584 | 89 | 74 |
| AR542 | 61 | 60 |
| AR502 | 79 | 33 |
| LSD 5% | 10 | |

Time periods of longer than 3 days were also tested and gave proportionally similar results as above however, with reduced rates of endophyte viability.

Conclusion

The data strongly supports the contention that AR584 has unique properties compared to other endophytes in retaining seed viability characteristics when plants are treated with fungicides during seed development. AR584 was found to be more robust to fungicides of different chemical activities, especially to the fungicide "Opus®".

AR584 was also found to have increased resistance to extremes in heat and humidity when compared to other endophytes.

Trial 2

Introduction

This trial was done to supplement the results shown in trial one. The tolerance of two endophytes, AR584 and AR542 in two tall fescue cultivars, 'Jesup' and 'Georgia 5' when treated with three different fungicide treatments was tested.

The fungicide treatments tested included:
1. Nil treatment
2. Opus only applied at 1.0 L/ha; and
3. a mixture of Opus® and Amistar® applied at 0.5+0.5 L/ha The accelerated ageing (AA) process was also adapted. As discussed above in trial 1, AA was undertaken by incubating seeds at a high temperature of 40° C. and 100% Relative Humidity (RH).

Method

Field Trial

A field trial was conducted on two tall fescue cultivars, 'Jesup' and 'Georgia 5' that were inoculated with the two endophytes AR584 and AR542. The field trial was carried out as described above in Trial one, wherein the plants of were inoculated with endophyte and then transplanted into trial plots. Each plot consisted of 4 plants of each cultivar, in rows 1.0 m apart. Treatments were replicated three times in a randomised block design.

Fungicides

Three fungicide treatments where trialed as outlined below:
1. Nil treatment;
2. Opus@ only (O), applied at 1.0 L/ha; and
3. a mixture of Opus@ applied at 0.5 L/ha and Amistar@ (O+A) applied at 0.5 L/ha.

Again, the doses used were the approximately the recommended label rates for use of the above products. The timing of the fungicide application was as per those recommended to growers and coincides with the period of most disease pressure in crops.

The accelerated ageing, Endophyte Assessment by Grow-out test, Endophyte detection and Statistical Analysis was also carried out as outlined above in Trial 1.

Results

Endophyte and Fungicide Effect

Figure 3:
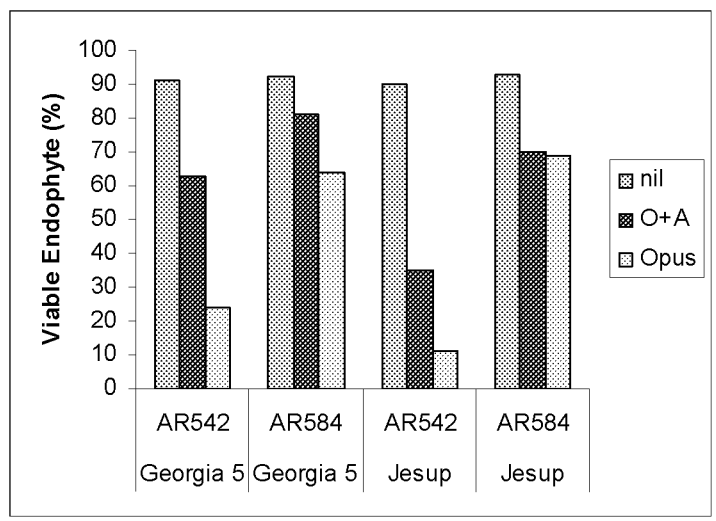

FIG. 3 and Table 6 shows the viability of each endophyte when treated with the various fungicide treatments. As shown, AR584 had 81% viability when treated with a mixture of Opus@ and Amistar@ (O+A) and 64% viability when treated with Opus@ (O) only in the Georgia 5 cultivar. The endophyte viability for the Jesup cultivar was 70% and 69% for the respective treatments. In comparison, AR542 had 63% and 24% viability in the Georgia 5 cultivar and 35% and 11% viability in the Jesup cultivar.

These results show that there was a clear difference in endophyte viability of both endophytes after the treatment of the various fungicides.

TABLE 6

The percentage of viable endophyte for AR542 and AR584 in two cultivars (Georgia 5 and Jesup) when treated with: no fungicide, Opus ® + Amistar ® (O + A) fungicide or Opus ® (O) fungicide alone.

| Cultivar | Endophyte | Fungicide treatment | | |
|---|---|---|---|---|
| | | nil | O + A | Opus |
| Georgia 5 | AR542 | 91 | 63 | 24 |
| Georgia 5 | AR584 | 92 | 81 | 64 |
| Jesup | AR542 | 90 | 35 | 11 |
| Jesup | AR584 | 93 | 70 | 69 |
| | LSD 5% | | 11.6 | |

When the averages of the percentage viability of the different entophytes are compared across the treatments and cultivars, the difference between AR584 and AR542 as shown in Table 7, is highly significant. The data shows that AR584 endophyte has a higher viability of 76% compared to AR542, which had 54% viability across the different cultivar and fungicide treatments.

TABLE 7

Endophyte for data averaged over the different cultivar, fungicide and accelerated aging.

| Endophyte | E + % |
|---|---|
| AR584 | 76 |
| AR542 | 54 |
| LSD 5% | 13 |
| F prob | <0.001 |

There was no difference in the level of viable endophyte for both AR548 and AR542 endophytes for nil fungicide treatment. However, when the fungicide Opus@ was applied, there was a significant interaction of P<0.001. As shown in Table 8 below, when AR584 endophyte inoculated plants where treated with Opus®, the viable endophyte level (average of nil and 3 day AA) dropped to 60%. In contrast AR542 for the same treatment was 17%.

TABLE 8

Percentage viability of endophyte for AR584 and AR542 endophyte
and treatment of Opus ® fungicide.

|        | nil    | Opus   |
|--------|--------|--------|
| AR584  | 93     | 60     |
| AR542  | 91     | 17     |
| LSD 5% | 9.2    |        |
| F prob | <0.001 |        |

Cultivar Effect

Table 9 below shows that there was also a significant interaction (P=0.045) between the endophyte, cultivar and fungicide. This interaction is the result of the Opus@ fungicide treatment, which considerably dropped the level of viable endophyte. The percentage result of this was less in Georgia cultivar in comparison to the Jesup cultivar.

However, this difference between AR584 endophyte and the AR542 endophyte in comparison to the cultivar type was comparable over both treatments.

TABLE 9

Shows the interaction between the various
Endophyte, Cultivar and Fungicide.

|          |           | AR584 |      | AR542 |      |
|----------|-----------|-------|------|-------|------|
|          | Fungicide | nil   | Opus | nil   | Opus |
| Cultivar | Georgia 5 | 93    | 64   | 91    | 24   |
|          | Jesup     | 93    | 55   | 91    | 11   |
|          | LSD 5%    | 18.4  |      |       |      |
|          | F prob    | 0.045 |      |       |      |

Conclusion

This trial showed that the AR584 endophyte was more robust than AR542 endophyte when treated with various fungicide treatments. As shown, the AR584 endophyte had an improved tolerance to the various fungicide treatments, when compared to AR542 endophyte. This relationship was the same in both tall fescue cultivars tested.

This robustness is particularly evident when tall fescue combined with AR584 endophyte was exposed to Opus®, a triazole rust control fungicide.

Trial 3

To test whether or not endophytes can be transferred to other species of grass besides Jesup and Georgia 5, results are now included for a different endophyte, AR1 showing that this endophyte can be inoculated into cultivars 'Grasslands Advance' type grass and Kentucky 31 tall fescues.

Inoculation data for inter-species inoculation of AR1 (*Neotyphodium lolii*) into Tall Fescue *(*Schedonorus phoenix*) and Meadow Fescue (*Festuca pratensis*) hosts. (*previously *Festuca arundinacea*)

Tall Fescue:

| plant | fungus | pos | neg | dead | % positive live |
|-------|--------|-----|-----|------|-----------------|
| 949   | AR1    | 19  | 24  | 20   | 44              |
| K31   | AR1    | 26  | 53  | 37   | 33              |

949 = four replicates of 10-18 plants
K31 = seven replicates of 10-19 plants

Meadow Fescue:

| plant | fungus | pos | neg | dead | % positive live |
|-------|--------|-----|-----|------|-----------------|
| J103  | AR1    | 2   | 5   | 13   | 29              |
| J110  | AR1    | 3   | 27  | 37   | 10              |

J103 = one replicate of 20 plants
J110 = six replicates of 4-2-plants

It should be appreciated from the above that there is provided an improved endophyte which in combination with a plant cultivar, addresses problems associated with current turf management practice and transport issues.

Aspects of the present invention have been described by way of example only and it should be appreciated that modifications and additions may be made thereto without departing from the scope thereof.

REFERENCES

Bluett, S. J.; Thom, E. R.; Clark, D. A.; Waugh, C. D. '*Effects of a novel ryegrass endophyte on pasture production, dairy cow milk production and calf liveweight gain*' Australian Journal of Experimental Agriculture, Vol. 45 No. 1 Pages 11-19 (2005).

Hill, N S; Brown E; 'Endophyte viability in seedling tall fescue treated with fungicides' Crop Science, September-October, 2000, vol. 40, no. 5, p. 1490-1491, ISSN: 0011-183X (Abstract Only).

Meriaux B, Leyronas C, Deneufbourg F 'Effect of fungicides and heat treatment on seed germination of endophyte infected perennial ryegrass' Multifunction grasslands, Organizing Committee of the European Grassland Federation (Abstract only).

Park, J H; Choi, G J; Lee, S W; Jang, K S; Lim, H K; Chung, Y R; Cho, K Y; Kim, J C 'Isolation and characterisation of *Burkholderia cepacia* EB215, an endophytic bacterium showing a potent antifungal activity against *Colletotrichum* species' Korean Journal of Microbiology and Biotechnology, 33/1 (16-23), ISSN-1598-642X, 2005, (Abstract Only).

Rolston, M. P; Archie, W J; Simpson, W R; 'Tolerance of AR1 Neotyphodium endophyte to fungicides used in perennial ryegrass seed production' New Zealand Plant Protection Volume 55, 2002. Proceedings of a conference, Centra Hotel, Rotorua, New Zealand, 13-15 Aug. 2002; pp 322-326; Publisher: New Zealand Plant Protection Society; Rotorua; New Zealand.

Saiga, S; Kodama, Y; Takahashi, H; Tsuiki, M; 'Endophyte removal by fungicides from ramets of perennial ryegrass and tall fescue' 2003 Grassland Science.

What we claim is:

1. A method of treating fungi infection in a grass plant whilst maintaining grass resistance to pests by the steps of:
    (a) inoculating of grass seed with AR584 endophyte (AGAL deposit no. NM98/04676 dated 12 May 1998);
    (b) growing the grass and endophyte combination; and
    (c) subjecting the grass to treatment with fungicide;
    and wherein the grass retains resistance to pests after fungicide treatment.

2. The method of claim 1 wherein at least 50% endophyte viability is retained after fungicide treatment.

3. The method of claim 1 wherein the fungicide selected from: the triazole group, the strobilurin group, and combinations of these two fungicide groups.

4. The method as claimed in claim 1 wherein the fungicide is applied at flowering of the grass plant.

5. The method as claimed in claim 1 wherein the grass is a tall fescue variety.

6. A method of maintaining or avoiding significant loss in endophyte viability in grass seed due to exposure of the seed to elevated temperature, elevated humidity or both, by the steps of:
   (a) inoculating the grass with AR584 endophyte (AGAL deposit no. NM98/04676 dated 12 May 1998);
   (b) subjecting the grass to treatment with fungicide;
   (c) collecting seeds from the inoculated grass; and
   (d) subjecting the grass seed to elevated temperature, elevated humidity or both.

7. The method as claimed in claim 6 wherein greater than 50% endophyte viability is maintained in the grass seed.

8. The method as claimed in claim 6 wherein at least 50% viable endophyte is maintained after the seed is subjected to temperatures of between 15° C. and 55° C. for a time period of at least 3 days.

9. The method as claimed in claim 6 wherein the seed at least 50% viable endophyte is maintained after the seed is subjected to a relative humidity of 70% or greater for at least 3 days.

10. The method as claimed in claim 6 wherein the seed retains at least 60% endophyte viability after the seed is subjected to a temperature of up to 40° C. and a relative humidity of up to 100% for at least a time period of 3 days.

11. The method as claimed in claim 6 wherein the grass is a tall fescue variety.

12. A method of maintaining or avoiding significant loss in endophyte viability during transportation of grass seed inoculated with endophyte by the steps of:
    (a) inoculating the grass with AR584 endophyte (AGAL deposit no. NM98/04676 dated 12 May 1998);
    (b) subjecting the grass to treatment with fungicide;
    (c) collecting seeds from the inoculated grass; and
    (d) transporting the seeds, wherein the seeds are subjected to elevated temperatures, elevated humidity or both during transportation.

13. The method as claimed in claim 12 wherein greater than 50% endophyte viability is maintained in the grass seed after transportation.

14. The method as claimed in claim 12 wherein at least 50% viable endophyte is maintained after the seed is subjected to temperatures of between 15° C. and 55° C. for a time period of at least 3 days.

15. The method as claimed in claim 12 wherein at least 50% viable endophyte is maintained after the seed is subjected to a relative humidity of 70% or greater for at least 3 days.

16. The method as claimed in claim 12 wherein the seed retains at least 60% endophyte viability after the seed is subjected to a temperature of up to 40° C. and a relative humidity of up to 100% for at least a time period of 3 days.

17. The method as claimed in claim 12 wherein the grass is a tall fescue variety.

18. The method as claimed in claim 1 wherein at least 65% or greater endophyte viability is retained when the combination is sprayed with a 50:50 wt/wt combination of triazole based fungicide and strobilurin based fungicide.

19. The method as claimed in claim 1 wherein the grass is a synthetic grass cultivar.

\* \* \* \* \*